United States Patent [19]

Schmidt

[11] Patent Number: 4,469,903
[45] Date of Patent: Sep. 4, 1984

[54] PROCESS FOR THE PRODUCTION OF ISOPROPYL ALCOHOL

[75] Inventor: Robert J. Schmidt, Rolling Meadows, Ill.

[73] Assignee: UOP Inc., Des Plaines, Ill.

[21] Appl. No.: 534,226

[22] Filed: Sep. 21, 1983

[51] Int. Cl.³ .................... C07C 29/86; C07C 29/80; C07C 29/04
[52] U.S. Cl. ...................................... 568/918; 44/53; 568/899; 568/916
[58] Field of Search ........................ 568/916, 918, 899

[56] References Cited

U.S. PATENT DOCUMENTS

| | | | |
|---|---|---|---|
| 2,010,686 | 8/1935 | Bent et al. ............................ | 568/918 |
| 3,328,469 | 6/1967 | Spector et al. ....................... | 260/641 |
| 3,455,664 | 7/1969 | Rosscup et al. ...................... | 568/918 |
| 3,990,952 | 11/1976 | Katzen et al. ......................... | 203/33 |
| 3,994,983 | 11/1976 | Webers et al. ....................... | 260/641 |
| 4,161,429 | 7/1979 | Baiel et al. ............................. | 203/18 |
| 4,251,231 | 2/1981 | Baird ..................................... | 568/918 |
| 4,267,397 | 5/1981 | Schmidt et al. ...................... | 568/899 |
| 4,281,206 | 7/1981 | Brandes et al. ...................... | 568/396 |
| 4,340,769 | 7/1982 | Brandes et al. ...................... | 568/899 |
| 4,349,415 | 9/1982 | DeFilippi et al. .................... | 568/918 |
| 4,352,945 | 10/1982 | Bezman ............................... | 568/899 |
| 4,382,843 | 5/1983 | Black ..................................... | 203/19 |
| 4,403,999 | 9/1983 | Bezman ............................... | 568/918 |

OTHER PUBLICATIONS

Hydrocarbon Processing, Nov. '67, vol. 46, No. 11, p. 194, "Isopropanol" (BP Chemicals [U.K.] Ltd.), Stone & Webster Engineering Corp.
Hydrocarbon Processing, Nov. '67, vol. 46, No. 11, p. 195, "Isopropanol", Hibernia-Chemie GmbH.
Hydrocarbon Processing, Nov. '81, p. 173, "Isopropanol", Deutsche Texaco AG.

Primary Examiner—J. E. Evans
Attorney, Agent, or Firm—James R. Hoatson, Jr.; John F. Spears, Jr.; William H. Page, II

[57] ABSTRACT

A process is disclosed for the production of aliphatic alcohol by the direct hydration of an olefinic hydrocarbon. The process is directed to the production of isopropyl alcohol. The process includes the recovery of the alcohol from a water-rich hydration zone effluent stream by countercurrent liquid-liquid extraction against a paraffinic solvent. The solvent is derived from paraffins originally admixed with the olefin-containing feed stream, and the raffinate stream comprises water which is recycled in the process. Expensive product fractionation is eliminated in the production of a fuel grade isopropyl alcohol.

14 Claims, 1 Drawing Figure

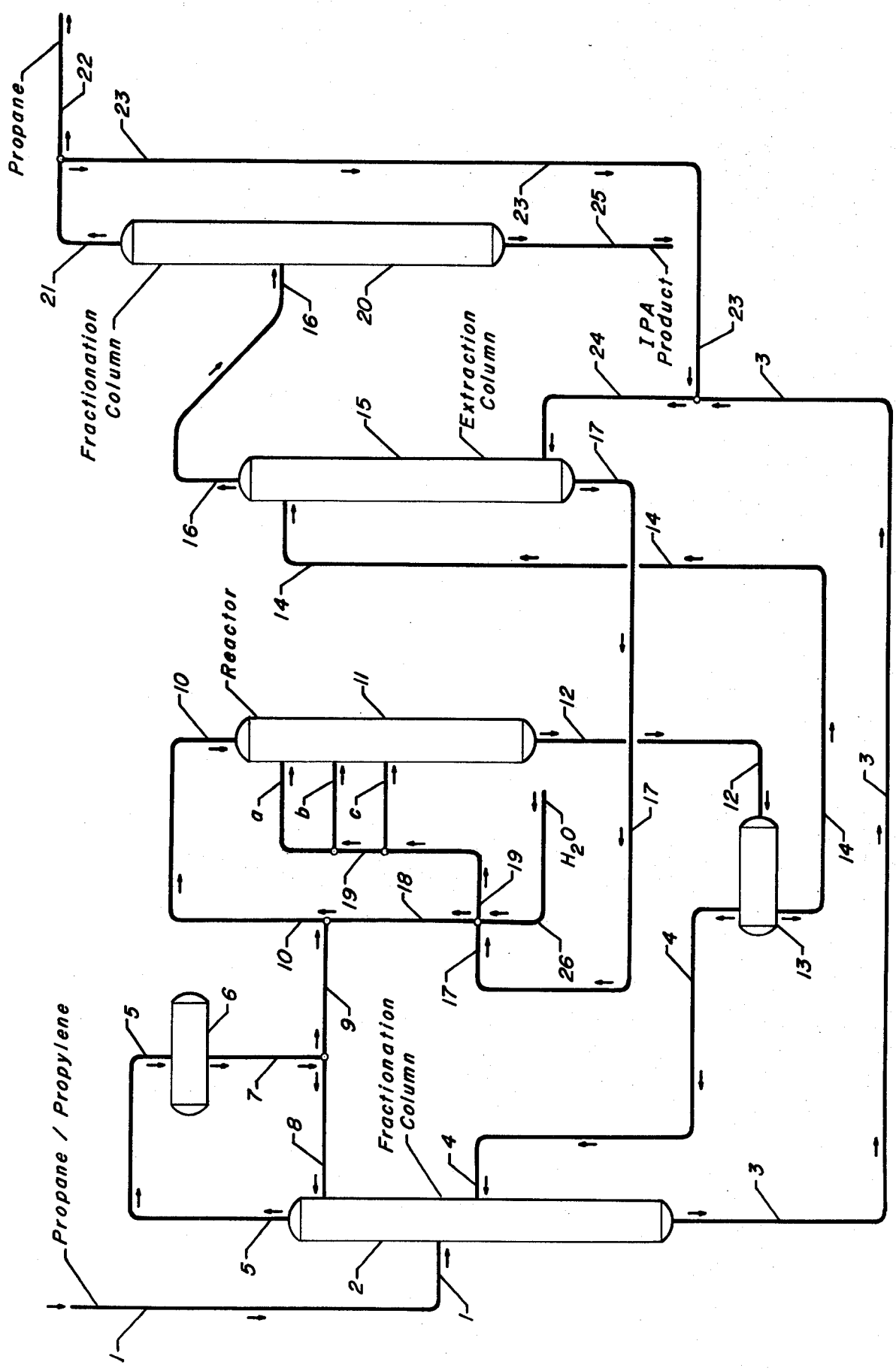

PROCESS FOR THE PRODUCTION OF ISOPROPYL ALCOHOL

BACKGROUND OF THE INVENTION

The invention relates in general to the recovery of a desired product in a hydrocarbon conversion process. More specifically, the invention relates to a process for the production of an aliphatic alcohol by the hydration of an olefinic hydrocarbon. The preferred embodiment of the process is the production of isopropyl alcohol by the reaction of propylene with water, with the product isopropyl alcohol being recovered from a liquid phase hydration zone effluent stream through the use of liquid-liquid extraction rather than the conventional fractionation methods. A preferred use of the subject process is the production of a fuel grade isopropyl alcohol which may be blended directly into a gasoline.

PRIOR ART

The synthetic production of isopropyl alcohol is a well established commercial industry. Among the earliest processes for the production of isopropyl alcohol were the so-called indirect hydration processes. A basic form of this type of process comprises the reaction of the olefin with sulfuric acid of various concentrations to produce alkylsulfates which are then hydrolyzed to produce the corresponding alcohols. The process flow illustrated on page 194 of the November, 1967 issue of *Hydrocarbon Processing* is believed representative of this type of isopropyl alcohol synthesis process. This type of process has various problems such as the corrosiveness of the sulfuric acid and various compounds present in the process, high chemical consumption, significant by-product formation and a generally complicated process flow. These shortcomings have prompted the development of the so-called direct hydration processes.

In the direct hydration process, a feed olefinic hydrocarbon such as propylene is directly reacted with water to produce the product alcohol. One early form of this direct hydration is described in U.S. Pat. No. 3,328,469 (Spector et al.). This patent teaches that the isopropyl alcohol may be recovered from a vapor phase reactor effluent by scrubbing the effluent in a packed tower with water. The resultant aqueous isopropyl alcohol solution is withdrawn from the bottom of the scrubber and fed to a distillation zone. In a first fractionation column, water is separated as a bottom fraction. The overhead, comprising an azeotropic mixture of isopropyl alcohol, is then sent to a second distillation column for the removal of impurities such as propylene and isopropyl halides. For the manufacture of anhydrous isopropyl alcohol, the reactor effluent is condensed and subjected to a phase separation procedure. An isopropyl alcohol-containing phase is removed from the separation and passed into a distillation zone. The recovery of isopropyl alcohol by fractionation in a similar direct hydration process is illustrated in the diagram presented at page 195 of the November, 1967 issue of *Hydrocarbon Processing*. The current development work in the area of direct hydration catalyst appears to be centered on the use of ion exchange resins. A particularly preferred type of such resin is described in U.S. Pat. No. 4,340,769 (Brandes et al.).

U.S. Pat. Nos. 3,994,983 (Webers et al.) and 4,281,206 (Brandes et al.) are pertinent for their teaching of the reaction zone configurations, conditions, and techniques which may be employed for the direct hydration of propylene.

A flow diagram of the reaction section and the fractionation section of a contemporary process for the production of isopropyl alcohol is presented at page 173 of the November, 1981 issue of *Hydrocarbon Processing*. In this flow scheme, the propylene and water are passed into a reactor, with water also being injected at intermediate points along the length of the reactor. The reactor effluent is a liquid phase stream which is passed into a vapor-liquid separation zone. Vapors from this separation zone are passed to a propylene recovery zone in which the propylene is separated from propane. The liquid phase from the separation zone is charged to a distillation column from which the diisopropyl ether by-product is removed overhead. The bottoms of the first column are charged to a second column in which isopropyl alcohol is taken overhead as an aqueous azeotropic mixture. Dehydration of the azeotropic mixture is carried out using benzene as an entrainer. Water removed as a bottoms product from the second column is internally recycled within the process.

A significant body of art has developed on the separation of isopropyl alcohol from reaction mixtures through the use of extractive distillation techniques. One example is provided in U.S. Pat. No. 4,267,397 (Schmidt et al.). U.S. Pat. Nos. 4,161,429 (Baiel et al.) and 3,990,952 (Katzen et al.) are believed representative of such azeotropic separation techniques.

U.S. Pat. No. 4,352,945 (Bezman) describes a multistep process in which isopropyl alcohol is produced through the direct hydration of propylene using a resin-type catalyst. In this process, the liquid phase effluent from the hydration reactor is passed into a first distillation column operated at conditions which produce an overhead product which is an azeotrope primarily containing diisopropyl ether and a bottom stream containing primarily isopropyl alcohol and water. The bottom stream of the first column is passed into a second distillation column. The second column produces an isopropyl alcohol-water azeotrope which is removed as an overhead stream. The isopropyl alcohol is then recovered from this azeotropic mixture. The reference indicates a number of methods may be utilized for this recovery, with the preferred method comprising the admixture of the isopropanol-containing azeotrope with a gasoline blending hydrocarbon stream. The isopropyl alcohol is thereby extracted from the azeotrope. However, this extraction occurs after two distillation operations, and the aqueous phase present after the extraction is apparently characterized as comprising only 0.1 vol. % of the total liquids present.

U.S. Pat. No. 4,382,843 (Black) describes a method of recovering ethanol from a dilute aqueous solution. The crude ethanol solution is first subjected to extractive distillation. An alcoholic mixture from the extractive distillation column is then fed to a fractionation column. Ethanol is recovered by extraction into a heated gasoline boiling range hydrocarbon mixture.

BRIEF SUMMARY OF THE INVENTION

The subject invention is a process for the production of $C_2$ to $C_5$ aliphatic alcohols which reduces the cost of recovering the product alcohol from the effluent stream of the hydration zone. In the subject process, only a single fractionation column is required to recover a useful isopropyl alcohol product stream from the hydration zone effluent stream. The improved process comprises the unique step of contacting the hydration zone effluent stream with propane or a similar corresponding hydrocarbon in a countercurrent liquid-liquid extraction zone. The isopropyl alcohol and hydration reaction by-products are thereby transferred to the propane stream from which they are recovered by simple fractionation.

One broad embodiment of the invention may be characterized as comprising the steps of contacting propylene with a molar excess of water and with a solid hydration catalyst in a reaction zone and thereby producing a liquid phase hydration zone effluent stream which comprises water and isopropyl alcohol; passing at least a liquid phase portion of the hydration zone effluent stream into a liquid-liquid extraction zone wherein this portion of the hydration zone effluent stream is contacted with a propane solvent stream and thereby forming an extract stream which comprises the isopropyl alcohol and propane; separating the isopropyl alcohol from the propane of the extract stream by fractional distillation, recycling at least a portion of the thus-separated propane to the extraction zone, and withdrawing the aliphatic alcohol.

BRIEF DESCRIPTION OF THE DRAWING

The drawing is a simplified process flow diagram of a preferred embodiment of the invention.

The drawing has been simplified by the elimination of various pieces of standard processing equipment such as vessel internals, control systems, pumps, compressors, startup lines, etc. This description of one embodiment of the invention is not intended to preclude from the scope of the invention those other embodiments set out herein or which result from the normal and expected modification of those embodiments. Referring now to the drawing, a feed stream comprising an admixture of propane and propylene enters the process through line 1 and is passed into an intermediate point of a single fractional distillation column 2 employed as a propylene-propane splitter. Propylene which enters the column 2 is concentrated into the overhead vapor stream removed in line 5 which passes through an overhead condenser not shown wherein it is condensed to form a liquid collected in the overhead receiver 6. Propylene is removed from the overhead receiver in line 7 and divided into a first portion which is returned to the column 2 through line 8 as reflux and a second portion which is passed to the hydration reactor via line 9. Propylene flowing through line 9 is admixed with water from line 18 and passed into the hydration reactor 11 through line 10. The water and propylene pass downward through a hydration catalyst retained within the reactor, with additional portions of water from line 19 being added at various points along the length of the reactor as quench streams fed through lines a, b, and c.

A liquid phase stream comprising the large molar excess of water fed to the reactor, isopropyl alcohol, and reaction by-products such as acetone and diisopropyl ether is removed from the hydration reactor through line 12 and passed into a vapor-liquid separation vessel 13. This vessel is maintained at a lower pressure than the hydration reactor and a vapor phase stream comprising propane and propylene therefore separates from the entering liquid. This vapor phase stream is passed into the fractionation column 2 through line 4. Vapors may also be withdrawn from the reactor 11 through a line not shown and passed into the fractionation column. An aqueous stream comprising the reaction products is transferred from the separation vessel to the top of a countercurrent extraction column 15 through line 14. This entering aqueous phase passes downward through the extraction column countercurrent to an ascending stream of propane. Isopropyl alcohol and other reaction products are transferred to the propane stream from the aqueous stream. This produces an aqueous raffinate stream removed from the bottom of the extraction column in line 17. This stream preferably passes through a water treatment zone not shown and is then recycled to the reactor through line 17. Makeup water is charged to the process through line 26.

The extract stream removed from the top of the extraction column in line 16 comprises the propane solvent and extracted isopropyl alcohol and other reaction products. The extract stream is passed into a second fractional distillation column 20. This column is operated under conditions which effect the separation of the entering compounds. A net bottom stream which comprises substantially all of the entering isopropyl alcohol is removed as a product stream of the process through line 25. Propane is separated into a net overhead vapor stream removed in line 21. This propane is divided into a first portion which is removed through line 22 and discharged from the process and a second portion which is recycled to the extraction column through line 23. The solvent employed in the extraction column comprises the admixture of the propane removed from the fractionation column 2 as a net bottom stream carried by line 3 and the propane stream carried by line 23. This admixture is passed into the bottom of the extraction column through line 24.

DETAILED DESCRIPTION

Lower molecular weight aliphatic alcohols are valuable and widely used industrial chemicals. For instance, isopropyl alcohol may be used as a solvent in coatings and inks, as an antibacterial agent, and in cosmetics. The subject process may be utilized for the production of relatively high purity alcohol products such as would be used in these applications. However, the invention is basically directed to the production of a fuel grade isopropyl alcohol. Isopropyl alcohol is a desirable gasoline blending component due to its high octane number. When utilized for this purpose, the isopropyl alcohol may contain significant amounts of by-products, up to 5 or possibly 10 wt. %, such as ethers and ketones. The product alcohol stream may also normally be employed as a gasoline blending component when it contains a small amount of water. Water concentrations on the order of 0.5 wt. % are tolerable. The subject process may be applied to the production of a variety of $C_2$ to $C_5$ alcohols, but will be discussed primarily in terms of the preferred embodiment which is the production of isopropyl alcohol from propylene.

The contemporary technology is highly efficient at hydrating the feed olefinic hydrocarbon to a product alcohol. The methods presently known for separating the product alcohol from the effluent of the hydration zone are also highly advanced as to their effectiveness and operability. However, the present technology still depends on some form of fractional distillation or extractive distillation to recover the product alcohol from an aqueous stream. This is a very difficult separation to perform solely through fractional distillation. Fractional distillation columns are notoriously high consumers of utilities. These utilities include the heat required to vaporize liquid at the bottom of the fractional distillation column and the cooling requirements to condense overhead vapors. Significant utilities cost therefore remain in the operation of the process despite such engineering advances as heat exchange systems which greatly conserve heat within the product fractionation train. The column internals, reboilers, and overhead condensers employed on a fractional distillation column also represent significant capital expenditures.

It is an objective of the subject invention to provide an improved process for the production of $C_2$ to $C_5$ aliphatic alcohols. It is a further objective of the subject invention to provide a process for the production of isopropyl alcohol. It is a specific objective of the subject process to reduce the cost of recovering a product alcohol in a process in which the alcohol is produced by the direct hydration of an olefinic hydrocarbon. A further objective of the subject invention is to minimize the amount of fractional distillation necessary in the production of a fuel grade isopropyl alcohol.

The two chemical compounds charged to the subject process are water and an aliphatic olefin having from 2 to 5 carbon atoms per molecule. The feed olefinic hydrocarbon may therefore be chosen from ethylene, propylene, iso- and normal butenes, and various pentenes. The preferred feed olefinic hydrocarbon is propylene. If a high purity stream of the feed olefinic hydrocarbon is available, it may be charged directly to the hydration reaction zone. However, it is expected that the normal situation will involve the available feed stream containing a sizable amount of a relatively inert paraffinic hydrocarbon which has the same number of carbon atoms per molecule as the feed olefinic hydrocarbon. In these instances, it is preferred that the feed stream is passed into a first separation zone which preferably comprises a single fractional distillation column. Various recycle streams produced within the process are also preferably charged to this column. The olefin-containing feed stream charged to the first separation zone preferably contains at least 30 wt. % olefin. The first separation zone is operated at conditions which produce an olefin-rich process stream which is charged to the hydration reaction zone. Preferably, this stream, which enters the reactor, has an olefin concentration of at least 65 wt. %. Preferably, the concentration of the feed olefinic hydrocarbon in this stream is above 85 wt. %, and more preferably is above 90 wt. %. The presence of some of the inert paraffinic hydrocarbon in this stream is tolerable. This allows certain economies in the design and operation of the first separation zone. This separation will also produce a stream of the paraffinic hydrocarbon. As this hydrocarbon will eventually be discharged from the process, it is preferred that the concentration of the olefinic hydrocarbon is minimized in this stream. Therefore, this stream preferably contains less than 5 wt. % olefin.

The feed olefin is admixed with water and passed into the hydration reaction zone. Preferably, the hydration reaction zone comprises a single vertical tower-like vessel having suspended therein one or more beds of the solid hydration catalyst. Preferably, the reactor is operated as a trickle bed-type reactor with the olefin-water feed admixture entering the top of the reactor and passing downward through the catalyst to a void volume located in the lower portion of the reactor vessel. This void volume is preferably employed as a vapor-liquid separation zone. Vapors comprising the inert paraffin and any residual olefinic hydrocarbon may be withdrawn on a pressure control basis from this void volume. An aqueous phase collects in the bottom of the void volume and may be withdrawn on level control. The hydration reaction is exothermic, and it is therefore preferred that additional amounts of relatively low temperature water are injected into the descending reactants at several points along the height of the catalyst-containing zone within the reaction vessel.

The olefin-water feed admixture to the reaction vessel should contain at least a molar excess of water over that which is stoichiometrically required for the hydration reaction. The water concentration within the reaction zone is an important variable in the process. It is preferred that the molar ratio of water to entering olefinic hydrocarbon is between about 5:1 and 20:1. More preferably, this ratio is between about 8:1 and about 20:1. Each mole of the olefinic hydrocarbon charged to the reaction vessel therefore requires the addition of from about 8 to about 20 moles of water. Since only a small proportion of this water is consumed in the hydration reaction, the product alcohol is withdrawn from the hydration reaction vessel as a part of a relatively dilute aqueous alcohol solution. This dilution increases the cost of the prior art distillation methods of product recovery.

The hydration conditions which are suitable for the subject process include a pressure of from about 60 to about 200 atmospheres. Preferably, the hydration reactor is maintained at a pressure of from about 80 to about 125 atmospheres absolute. The hydration reaction zone is preferably operated at a temperature between about 120° and about 180° C. A preferred operating inlet temperature is between about 135° and about 160° C. These conditions are those which are preferred for the conversion of propylene to isopropyl alcohol. In this instance, it has been characterized as maintaining the propylene as a supercritical gas and the water as a liquid. Other conditions may be preferred with different feed olefin or with catalysts other than the preferred resin-type catalyst. The rate of water flow through the catalyst bed is preferably between about 1 and about 40 and preferably about 5 and about 25 moles of water per $cm^2$ of cross sectional area per hour. The liquid hourly space velocity of the entering olefinic hydrocarbon should be between about 0.05 and about 2, and is preferably between about 0.1 and 1.0.

As the subject invention basically relates to a method of recovering the alcoholic product, it is not limited to any particular hydration catalyst. The subject process may therefore be employed utilizing the presently preferred catalyst or those which are the result of the continuing research effort in this area. It is preferred that a solid particulate catalyst is employed. The presently preferred hydration catalysts are ion exchange catalysts or resins. The preferred resins comprise a copolymer of styrene and divinylbenzene. It is further preferred that these copolymer resins are treated with a sulfur-containing acid to yield a highly acidic sulfonic acid-containing resin. In general, the catalyst should contain from about 0.2 to 1 sulfonic acid group per aromatic ring present in the resin. These catalysts may be further modified as by chlorination, fluorination, etc., which has been shown to yield improved high temperature stability. A particularly preferred resin of this nature is described in the previously referred to U.S. Pat. No. 4,340,769, incorporated herein by reference. Suitable catalysts are available from commercial sources.

The aqueous stream withdrawn as the hydration zone effluent stream will contain an admixture of the product alcohol, water, paraffinic hydrocarbon which may be present in the feed stream, unreacted olefinic hydrocarbon, and the various possible reaction by-products such as ethers and ketones. It is preferred that this admixture is preferably subjected to one or more flash operations which generate a vapor phase comprising the more volatile components present in the effluent. This vapor phase will basically be an admixture of propane and propylene during the hydration of propylene. These vapors may be passed into the initial separation zone to recover the propylene. The product alcohol remains in the aqueous liquid phase portion withdrawn from the separation steps. Depending on the conditions desired for use within the hydration reaction zone and in the downstream liquid-liquid extraction zone, these flashing steps may be limited or eliminated. However, the use of one such flash separation is presently preferred.

The remaining liquid phase portion of the aqueous stream removed from the hydration reaction vessel is passed into an extraction zone. This zone preferably comprises a single vertical countercurrent extraction column. Suitable apparatus may be designed with a minimum of experimentation based on the known properties of the product alcohol and paraffinic hydrocarbons. The use of extraction equipment which employs mechanical mixing devices such as rotating disc contacting apparatus is not preferred. The preferred extraction vessel comprises a single tower containing at least ten horizontal perforated contacting trays. The pressure maintained within the extraction zone must be sufficient to maintain both liquid phases as liquids, but otherwise plays no important part in the operation of the extraction zone. It is preferred that the extraction is performed at a temperature between about 60° and about 122° F. (16°-50° C.). Those skilled in the art will recognize that the temperature chosen will have an effect upon the selectivity and absorption capacity of the solvent stream. The preferred solvent is normally a relatively pure stream of the paraffinic hydrocarbon which is charged to the process in admixture with the feed olefinic hydrocarbon. Therefore, in the hydration of propylene, the preferred solvent hydrocarbon is propane. However, in the instance of the hydration of ethylene, the preferred solvent is a readily available high purity paraffinic hydrocarbon which is less volatile than ethylene and meets the requirements of the subject process. It is preferred that the flow rate of the organic solvent phase is at least 10 times the flow rate of the alcohol entering the extraction zone. More preferably, the flow rate of the organic solvent phase is 20 times the rate at which the alcohol is charged to the extraction zone. The extraction zone should provide at least seven theoretical contacting stages. Suitable equipment for this extraction procedure may be selected from that equipment which has been utilized in similar extraction operations.

The effluent streams of the extraction zone are a raffinate stream and an extract stream. The raffinate stream is made up by those components of the extracted portion of the hydration zone effluent stream which do not become dissolved in the solvent. The raffinate stream is therefore basically water with a small amount of residual isopropyl alcohol and other compounds. The raffinate stream is preferably recycled within the process. The effluent of the extraction zone is suitable for passage into the hydration zone, although it may be necessary to remove certain impurities such as sodium or metal ions. This is basically to prevent detrimental effects to the hydration catalyst. If necessary, such water treatment may be performed using cation and anion exchangers. The extract stream removed from the extraction zone is made up of the entering solvent stream plus those compounds which have been transferred from the hydration zone effluent to the solvent stream. The extract stream therefore comprises an admixture of the solvent hydrocarbon, the product alcohol, and reaction by-products. In the preferred embodiment, the extract stream comprises an admixture of propane, isopropyl alcohol, acetone, and isopropyl ether.

The extract stream is passed into a second fractionation zone. Preferably, this fractionation zone is a single trayed fractionation column, although other types of fractionation equipment such as packed columns and the recently developed distillation devices which employ rotating internal elements may also be employed. When properly designed and operated, a distillation column containing about 20 real sieve trays will function adequately as this separation zone. This column will preferably have an external reflux system comprising an overhead condenser and receiver. The solvent material will be removed as the overhead product, with the paraffinic hydrocarbon preferably being withdrawn from the overhead system at a rate necessary to maintain the desired inventory of the solvent within the process. The remainder of the solvent is recycled back to the extraction column preferably after admixture with paraffinic hydrocarbon separated in the first fractionation column. Alternatively, the entire raffinate stream may be recycled to the extraction zone and a portion of the bottoms stream of the propane-propylene splitter may be rejected from the process. A net bottoms stream is removed from the reboiled second fractionation column and preferably withdrawn from the process. This bottoms stream is the isopropyl alcohol-containing product and may be passed to the appropriate gasoline blending facilities. In an alternative embodiment of the subject invention, this bottoms stream of the second fractionation column may be passed into additional fractionation columns wherein hydration by-products, such as ethers and ketones, may be separated by fractional distillation to thereby provide the high purity alcohol product. This variation can be employed when it is desired to produce a chemical grade alcohol rather than a fuel grade alcohol.

The subject process has the advantage of providing the desired isopropyl alcohol product without extensive energy-consuming separations such as difficult fractional distillation or extractive distillation. These undesired separation steps are replaced by a low cost liquid extraction followed by a relatively easy and therefore less expensive fractionation step. The reduction in utility cost provided by the process is accompanied by a reduction in capital costs and a simplification of the overall process flow. A preferred embodiment of the subject process may be characterized as a process for the production of isopropyl alcohol which comprises the steps of passing a feed stream comprising propane and propylene into a first fractionation zone, and withdrawing from the fractionation zone a first net overhead stream, which is rich in propylene, and a first net bottoms stream, which is rich in propane; passing the first net overhead stream and a water stream into a hydration zone containing a solid hydration catalyst and maintained at hydration-promoting conditions; withdrawing a liquid phase hydration zone effluent stream comprising water and isopropyl alcohol from the hydration zone; recovering isopropyl alcohol from the hydration zone effluent stream by contacting at least a liquid phase portion of the hydration zone effluent stream with a solvent stream comprising at least a portion of the first net bottoms stream in a liquid-liquid extraction zone maintained at extraction conditions and thereby forming an extract stream which comprises isopropyl alcohol and propane and a raffinate stream which is rich in water; and separating the extract stream in a second fractionation zone and thereby forming a second net bottoms stream, which is rich in isopropyl alcohol, and a second net overhead stream which is rich in propane, and withdrawing the second net bottoms stream from the process as a fuel grade isopropyl alcohol product stream.

I claim as my invention:

1. A process for the production of a $C_2$, $C_3$, $C_4$ or $C_5$ aliphatic alcohol which comprises the steps of:
   (a) contacting a feed olefinic hydrocarbon having 2, 3, 4 or 5 carbon atoms per molecule with a molar excess of water and with a solid hydration catalyst in a reaction zone and producing a liquid phase hydration zone effluent stream which comprises water and a $C_2$, $C_3$, $C_4$ or $C_5$ aliphatic alcohol;
   (b) passing at least a liquid-phase portion of the hydration zone effluent stream into a liquid-liquid extraction zone wherein said portion of the hydration zone effluent stream is contacted with a solvent comprising a paraffinic hydrocarbon having the same number of carbon atoms as the aliphatic alcohol, and thereby forming an extract stream which comprises the aliphatic alcohol and the paraffinic hydrocarbon; and
   (c) separating the aliphatic alcohol and the paraffinic hydrocarbon contained in the extract stream by fractionation, recycling at least a portion of the thus-separated paraffinic hydrocarbon to the extraction zone, and withdrawing the aliphatic alcohol.

2. A process for the production of a $C_3$ or $C_4$ aliphatic alcohol which comprises the steps of:
   (a) contacting a feed olefinic hydrocarbon having 3 or 4 carbon atoms per molecule with a molar excess of water and with a solid hydration catalyst in a reaction zone and producing a liquid phase hydration zone effluent stream which comprises water and a $C_3$ or $C_4$ aliphatic alcohol;
   (b) passing at least a liquid-phase portion of the hydration zone effluent stream into a liquid-liquid extraction zone wherein said portion of the hydration zone effluent stream is contacted with a solvent comprising a paraffinic hydrocarbon having the same number of carbon atoms as the aliphatic alcohol, and thereby forming an extract stream which comprises the aliphatic alcohol and the paraffinic hydrocarbon; and
   (c) separating the aliphatic alcohol and the paraffinic hydrocarbon contained in the extract stream by fractionation, recycling at least a portion of the thus-separated paraffinic hydrocarbon to the extraction zone, and withdrawing the aliphatic alcohol.

3. The process of claim 2 further characterized in that the aliphatic alcohol is isopropyl alcohol and the paraffinic hydrocarbon is propane.

4. The process of claim 3 further characterized in that the hydration catalyst comprises a cation exchange resin catalyst.

5. The process of claim 4 further characterized in that the hydration catalyst is a sulfonated styrene-divinylbenzene copolymer resin.

6. The process of claim 5 further characterized in that the hydration zone effluent stream is first flashed to release a vapor phase comprising propane and propylene, and the remaining liquid portion of the hydration zone effluent stream is passed into the extraction zone.

7. A process for the production of isopropyl alcohol which comprises the steps of:
   (a) passing a feed stream comprising propane and propylene into a first fractionation zone, and withdrawing from the fractionation zone a first net overhead stream, which is rich in propylene, and a first net bottoms stream, which is rich in propane;
   (b) passing the first net overhead stream and a water stream into a hydration zone containing a solid hydration catalyst and maintained at hydration-promoting conditions;
   (c) withdrawing a liquid phase hydration zone effluent stream comprising water and isopropyl alcohol from the hydration zone;
   (d) recovering isopropyl alcohol from the hydration zone effluent stream by contacting at least a portion of the hydration zone effluent stream with a solvent stream comprising at least a portion of the first net bottoms stream in a liquid-liquid extraction zone maintained at extraction conditions and thereby forming an extract stream which comprises isopropyl alcohol and propane and a raffinate stream which is rich in water; and
   (e) separating the extract stream in a second fractionation zone and thereby forming a second net bottoms stream, which is rich in isopropyl alcohol, and a second net overhead stream which is rich in propane.

8. The process of claim 7 further characterized in that at least a portion of the second net overhead stream is passed into the extraction zone as a part of the solvent stream.

9. The process of claim 8 further characterized in that substantially all of the first net bottoms stream is passed into the extraction zone as a part of the solvent stream.

10. The process of claim 9 further characterized in that substantially all of the raffinate stream is passed into the hydration zone.

11. The process of claim 10 further characterized in that the hydration zone effluent stream is reduced in pressure to release a vapor phase stream comprising propane and propylene, the remaining liquid portion of the hydration zone effluent stream is passed into the extraction zone, and the vapor phase stream is passed into the first fractionation zone.

12. The process of claim 10 further characterized in that the hydration catalyst comprises a cation exchange resin catalyst.

13. The process of claim 12 further characterized in that the cation exchange resin is a styrene-divinylbenzene copolymer.

14. The process of claim 12 further characterized in that the hydration catalyst comprises a sulfonated styrene-divinylbenzene copolymer.

* * * * *